(12) United States Patent
Al-Shammasi et al.

(10) Patent No.: US 12,076,062 B2
(45) Date of Patent: Sep. 3, 2024

(54) MODULAR INTRAMEDULLARY FIXATION DEVICES

(71) Applicant: KUWAIT UNIVERSITY, Safat (KW)

(72) Inventors: Ahmed Ali Al-Shammasi, Safat (KW); Yagoub Abdulrahman Al Sayed Hashim, Safat (KW)

(73) Assignee: KUWAIT UNIVERSITY, Safat (KW)

( * ) Notice: Subject to any disclaimer, the term of this patent is extended or adjusted under 35 U.S.C. 154(b) by 170 days.

(21) Appl. No.: 17/393,645

(22) Filed: Aug. 4, 2021

(65) Prior Publication Data

US 2023/0040945 A1  Feb. 9, 2023

(51) Int. Cl.
*A61B 17/72* (2006.01)

(52) U.S. Cl.
CPC .............................. *A61B 17/7283* (2013.01)

(58) Field of Classification Search
CPC .................................................. A61B 17/7283
USPC ...................................................... 606/62–68
See application file for complete search history.

(56) References Cited

U.S. PATENT DOCUMENTS

| 5,626,580 | A | 5/1997 | Brosnahan |
| 8,216,238 | B2 | 7/2012 | Medoff |
| 2007/0233098 | A1* | 10/2007 | Mastrorio ........... A61B 17/7065 606/86 A |
| 2011/0077651 | A1 | 3/2011 | Lozier et al. |
| 2012/0065638 | A1 | 3/2012 | Moore |
| 2013/0231665 | A1* | 9/2013 | Saravia .............. A61B 17/7266 606/63 |
| 2015/0133937 | A1* | 5/2015 | Benedict ............ A61B 17/7258 606/64 |
| 2020/0100821 | A1 | 4/2020 | Barry et al. |

FOREIGN PATENT DOCUMENTS

| FR | 2653006 A1 | 4/1991 |
| GB | 2268068 A | 1/1994 |

* cited by examiner

*Primary Examiner* — Eduardo C Robert
*Assistant Examiner* — Tara Rose E Carter
(74) *Attorney, Agent, or Firm* — Nath, Goldberg & Meyer; Joshua B. Goldberg (57) ABSTRACT

The modular intramedullary fixation device is a multi-piece bone fixation device for insertion into the medullary cavity of a bone. In one embodiment, the modular intramedullary fixation device is formed from a plurality of substantially Z-shaped modular elements, which are assembled together to a desired length and width. In additional embodiments, the modular intramedullary fixation device includes a proximal portion, a distal portion, and a connector for connecting the two portions to each other. The connector may be provided in a wide variety of configurations, including an adjustable connector for adjusting the length of the modular intramedullary fixation device. Each of the proximal and distal portions may further have an adjustable length.

6 Claims, 12 Drawing Sheets

MODULAR INTRAMEDULLARY FIXATION DEVICES

BACKGROUND

1. Field

The disclosure of the present patent application relates to medical and surgical devices, and particularly to modular intramedullary fixation devices for the fixation of bones.

2. Description of the Related Art

Intramedullary fixation devices (IMFDs), such as nails and rods, are used for the fixation of various bones, and are typically used in the femur, tibia, humerus, radius and ulna. Given the wide variety of sizes and shapes of bones between different patients, great care must be taken in selecting an intramedullary device of the proper size and shape, and also in the preparation of the bone to accommodate the intramedullary device. A number of highly invasive techniques are used to treat patients by utilizing fixation devices. It would be desirable to be able to replace the conventional standards of care with a fixation device which is more adaptable for use with a variety of different patients, and which would utilized less invasive techniques. Thus, modular intramedullary fixation devices solving the aforementioned problems are desired.

SUMMARY

The modular intramedullary fixation device is a multi-piece bone fixation device adapted for insertion into the medullary cavity of a bone. In one embodiment, the modular intramedullary fixation device has a proximal section and a distal section, and is formed from a plurality of substantially Z-shaped modular elements. Each of the substantially Z-shaped modular elements has a proximal flange and a distal flange. The distal flange of each of the substantially Z-shaped modular elements is secured to the proximal flange of an adjacent one of the substantially Z-shaped modular elements. A proximal end piece is secured to the proximal flange of a proximal-most one of the substantially Z-shaped modular elements, and a distal end piece is secured to the distal flange of a distal-most one of the substantially Z-shaped modular elements.

The proximal end piece and a first portion of the substantially Z-shaped modular elements define the proximal section of the modular intramedullary fixation device, and the distal end piece and a second portion of the substantially Z-shaped modular elements define the distal section of the modular intramedullary fixation device. In order to match the dimensions of the particular bone (e.g., the ulna), a maximum width of the proximal section may be greater than a maximum width of the distal section.

Each of the proximal and distal end pieces has a passage formed therethrough for receiving a corresponding screw. Additionally, the proximal flange of each of the substantially Z-shaped modular elements has a passage formed therethrough for receiving a corresponding screw. Similarly, the distal flange of each of the substantially Z-shaped modular elements has a passage formed therethrough for receiving a corresponding screw to secure the plurality of substantially Z-shaped modular elements, the proximal end piece and the distal end piece together.

In an alternative embodiment, the modular intramedullary fixation device is formed from a proximal portion, having opposed proximal and distal ends, and a distal portion having opposed proximal and distal ends. A distal circular flange is formed on the distal end of the proximal portion, and a proximal circular flange is formed on the proximal end of the distal portion. A circular plate, the distal circular flange and the proximal circular flange are each secured together, such that the circular plate is sandwiched therebetween. Each of the circular plate, the distal circular flange and the proximal circular flange has at least one passage formed therethrough for receiving at least one screw to secure the circular plate, the distal circular flange and the proximal circular flange together. In order to match the dimensions of the particular bone (e.g., the ulna), a maximum width of the proximal portion may be greater than a maximum width of the distal portion.

In another alternative embodiment, the modular intramedullary fixation device includes a proximal portion, having opposed proximal and distal ends, and a distal portion, having opposed proximal and distal ends. The proximal portion has a distal connector formed on the distal end thereof. The distal connector has an annular groove formed therein. Similarly, the distal portion has a proximal connector formed on the proximal end thereof. The proximal connector has an annular groove formed therein. A coupler is provided, having an internal proximal rib for engaging the annular groove formed in the distal connector, and an internal distal rib for engaging the annular groove formed in the proximal connector. A pair of brackets clamp the coupler, the distal connector and the proximal connector therebetween. Each of the brackets has at least one passage formed therethrough for receiving at least one screw to secure the pair of brackets together. In order to match the dimensions of the particular bone (e.g., the ulna), a maximum width of the proximal portion may be greater than a maximum width of the distal portion.

In a further alternative embodiment, the modular intramedullary fixation device includes a proximal portion, having opposed proximal and distal ends, with a distal connector formed on the distal end of the proximal portion, and a distal portion, having opposed proximal and distal ends, with a proximal connector formed on the proximal end of the distal portion. A proximal collar, having opposed proximal and distal ends, is provided for receiving the distal connector of the proximal portion. A distal annular flange is formed about the distal end of the proximal collar. Similarly, a distal collar, having opposed proximal and distal ends, is provided for receiving the proximal connector of the distal portion. A proximal annular flange is formed about the proximal end of the distal collar. The distal annular flange is secured to the proximal annular flange.

Each of the proximal and distal annular flanges may have at least one passage formed therethrough for receiving at least one screw to secure the proximal and distal annular flanges together. In order to match the dimensions of the particular bone (e.g., the ulna), a maximum width of the proximal portion may be greater than a maximum width of the distal portion.

In another alternative embodiment, the modular intramedullary fixation device includes a proximal portion, having opposed proximal and distal ends, with a distal connector formed on the distal end of the proximal portion, and a distal portion, having opposed proximal and distal ends, with a proximal connector formed on the proximal end of the distal portion. An annular collar, having opposed proximal and distal open ends, is provided such that the proximal open end receives the distal connector of the proximal portion, and the distal open end receives the proximal connector of the distal portion. The annular collar is formed from first and second semi-cylindrical portions secured to one another.

Each of the first and second semi-cylindrical portions has at least one passage formed therethrough for receiving at least one screw to secure the first and second semi-cylindrical portions together. In order to match the dimensions of the particular bone (e.g., the ulna), a maximum width of the proximal portion may be greater than a maximum width of the distal portion.

In a further alternative embodiment, the modular intramedullary fixation device includes a proximal portion having opposed proximal and distal ends and a proximal accordion linkage to adjust the length of the proximal portion. The modular intramedullary fixation device similarly includes a distal portion having opposed proximal and distal ends and a distal accordion linkage to adjust the length of the distal portion. A connector is provided for connecting the proximal end of the distal portion to the distal end of the proximal portion.

The proximal portion further includes a fixed shaft and a rotating shaft. A first end of the proximal accordion linkage is secured to the fixed shaft of the proximal portion, and a second end of the proximal accordion linkage is rotatably secured to the rotating shaft of the proximal portion. The second end of the proximal accordion linkage may include a threaded collar in threaded engagement with a threaded portion of the rotating shaft of the proximal portion. Similarly, the distal portion includes a fixed shaft and a rotating shaft. A first end of the distal accordion linkage is secured to the fixed shaft of the distal portion, and a second end of the distal accordion linkage is rotatably secured to the rotating shaft of the distal portion. The second end of the distal accordion linkage may be a threaded collar in threaded engagement with a threaded portion of the rotating shaft of the distal portion.

The connector may be adjustable to adjust the overall length of the modular intramedullary fixation device. In this embodiment, the connector includes a threaded cylinder having opposed distal and proximal ends, with the proximal end of the threaded cylinder secured to the distal end of the proximal portion, and a rotating collar having opposed open distal and proximal ends, where the rotating collar has an internal threaded surface for threadedly engaging the threaded cylinder. The open distal end of the rotating collar has a plurality of teeth formed therearound. The connector further includes a rod partially received within the rotating collar and extending through the open distal end thereof. The rod has opposed distal and proximal ends, with the distal end of the rod being secured to the proximal end of the distal portion. A gear is rotatably mounted on the rod, with the gear engaging the plurality of teeth of the rotating collar. The user may rotate the gear to drive rotation of the rotating collar which, through its threaded engagement with the threaded cylinder, moves with respect to the threaded cylinder. In this way, the user may adjust the overall length of the modular intramedullary fixation device.

Alternatively, the connector may be provided in the form of a distal connector portion secured to the proximal end of the distal portion, where the distal connector portion has a threaded engaging member, and a proximal connector portion secured to the distal end of the proximal portion, where the proximal connector portion has a threaded passage for threadedly receiving the threaded engaging member.

These and other features of the present disclosure will become readily apparent upon further review of the following specification and drawings.

BRIEF DESCRIPTION OF THE DRAWINGS

FIG. 1.6 is a perspective view of another alternative embodiment of the modular intramedullary fixation device.

Similar reference characters denote corresponding features consistently throughout the attached drawings.

DETAILED DESCRIPTION OF THE PREFERRED EMBODIMENTS

Figure 1:
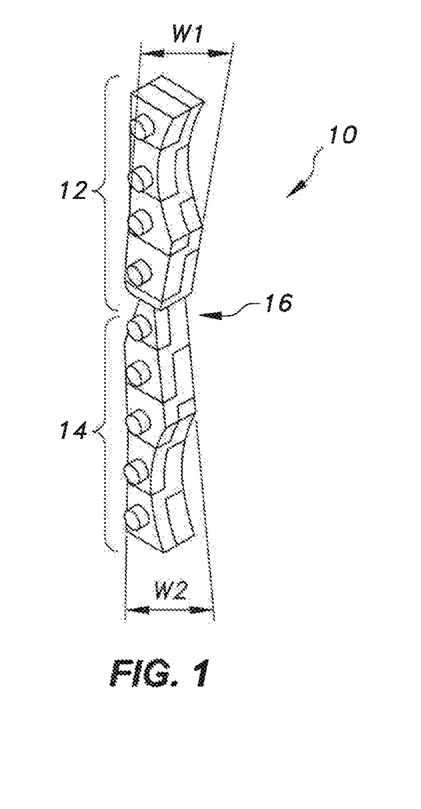
FIG. 1 is a perspective view of a modular intramedullary fixation device.
Figure 2:
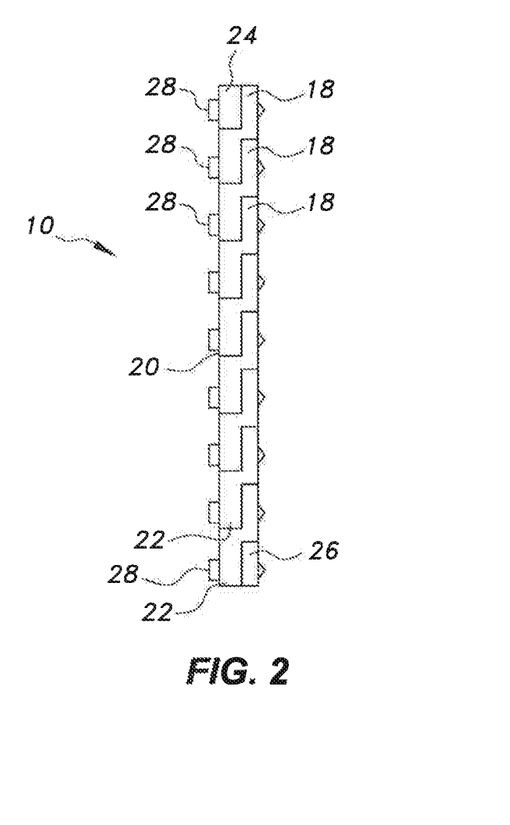
FIG. 2 is a side view of the modular intramedullary fixation device of FIG. 1.
Figure 3:
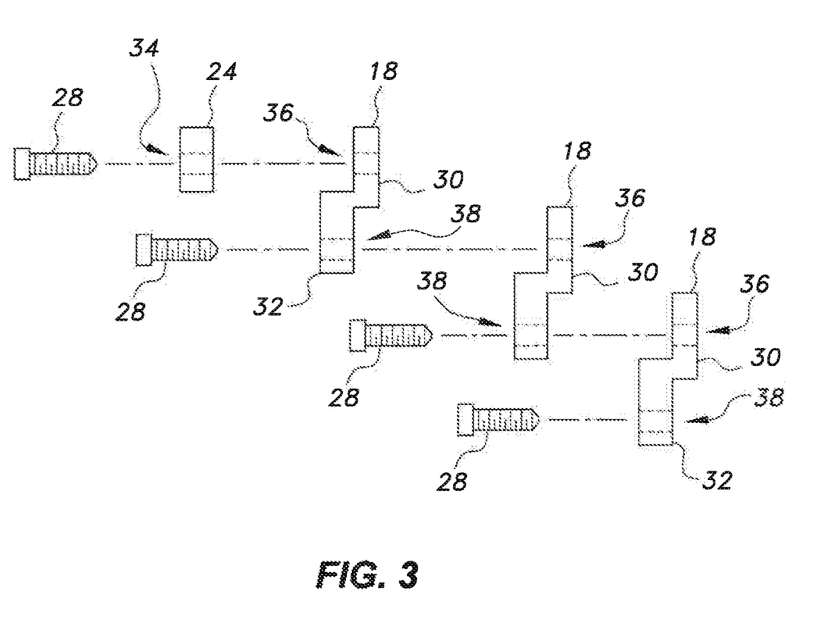
FIG. 3 is an exploded, partial side view of the modular intramedullary fixation device of FIG. 1.

The modular intramedullary fixation device 10 is adapted for insertion into the medullary cavity of a bone. In the embodiment of FIGS. 1-3, the modular intramedullary fixation device 10 has a proximal section 12 and a distal section 14, corresponding to the proximal and distal sections of the bone. The proximal section 12 is formed from a first portion of substantially Z-shaped modular elements 18, and the distal section 14 is formed from a second portion of substantially Z-shaped modular elements 22. The substantially Z-shaped modular elements 18 and 22 are substantially similar in design.

For purposes of simplification, only three of the substantially Z-shaped modular elements 18 are shown in FIG. 3, It should be understood that the method of joining the substantially Z-shaped modular elements 18, shown in FIG. 3, also applies to the substantially Z-shaped modular elements 22, and further applies to all substantially Z-shaped modular elements forming the modular intramedullary fixation device 10. It should be further understood that the number of substantially Z-shaped modular elements shown in FIGS. 1 and 2 is shown for exemplary purposes only, and that the total number of substantially Z-shaped modular elements may be varied in order to vary the length and width of the modular intramedullary fixation device 10 to match the particular bone of the particular patient.

As shown in FIG. 3, each of the substantially Z-shaped modular elements 18 has a proximal flange 30 and a distal flange 32. The distal flange 32 of each of the substantially Z-shaped modular elements 18 is secured to the proximal flange 30 of an adjacent one of the substantially Z-shaped modular elements 18. Additionally, a proximal end piece 24 is secured to the proximal flange 30 of a proximal-most one of the substantially Z-shaped modular elements 18, and a distal end piece 26 (shown in FIGS. 1 and 2) is secured to the distal flange of a distal-most one of the substantially Z-shaped modular elements 22.

The proximal end piece 24 and the first portion of the substantially Z-shaped modular elements 18 define the proximal section 12 of the modular intramedullary fixation device 10, and the distal end piece 26 and the second portion of the substantially Z-shaped modular elements 22 define the distal section 14 of the modular intramedullary fixation device 10. As shown in FIG. 1, in order to match the dimensions of the particular bone (e.g., the ulna), a maximum width W1 of the proximal section 12 may be greater than a maximum width W2 of the distal section 14.

Returning to FIG. 3, the proximal end piece 24 has a passage 34 formed therethrough for receiving a corresponding screw 28. Similarly, the distal end piece 26 also has a passage formed therethrough for receiving a corresponding one of the screws 28. Additionally, the proximal flange 30 of each of the substantially Z-shaped modular elements 18 has a passage 36 formed therethrough for receiving a corresponding one of the screws 28. Similarly, the distal flange 32 of each of the substantially Z-shaped modular elements 18 has a passage 38 formed therethrough for receiving a corresponding one of the screws 28. It should be understood that the substantially Z-shaped modular elements 22 also have similar passages for receiving corresponding ones of screws 28. Through insertion of screws 28 through aligned passages, the plurality of substantially Z-shaped modular elements 18, 22, the proximal end piece 24 and the distal end piece 26 together are secured together to form the modular intramedullary fixation device 10. It should be understood that screws 28 are shown for exemplary purposes only, and that bolts, rivets or any other suitable type of fixture may also be used to join the modular components together.

In FIGS. 1 and 2, each of the plurality of substantially Z-shaped modular elements 18, 22, a central substantially Z-shaped modular element 20 of a central section 16, the proximal end piece 24 and the distal end piece 26 are shown having an exemplary size and overall shape. It should be understood that the overall contouring and relative dimensions of each of these elements are shown for exemplary purposes only, and may be varied dependent upon the particular bone, particular procedure, particular circumstances, and particular patient.

Figure 4:
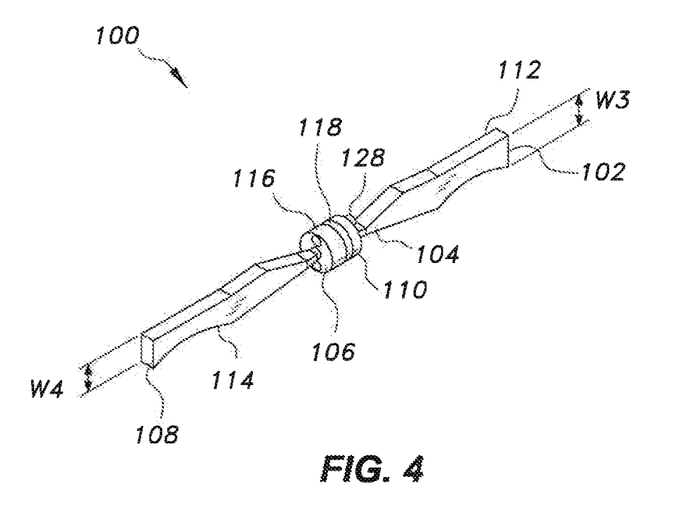
FIG. 4 is a perspective view of an alternative embodiment of the modular intramedullary fixation device.
Figure 5:
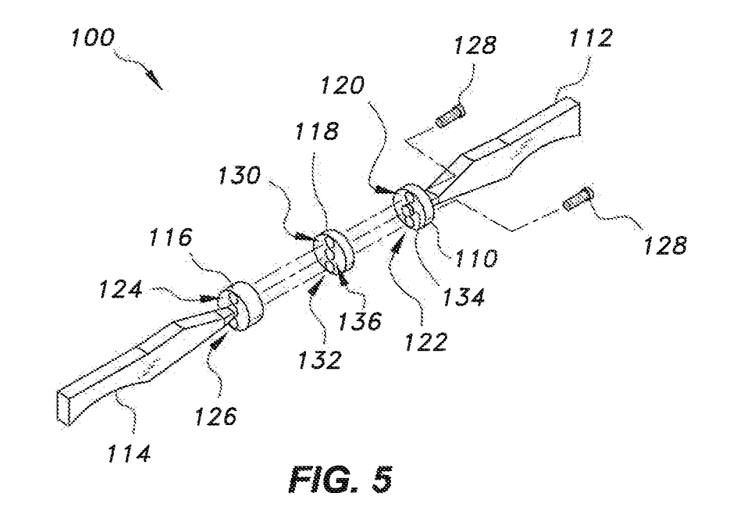
FIG. 5 is an exploded perspective view of the modular intramedullary fixation device of FIG. 4.

In the alternative embodiment of FIGS. 4 and 5, the modular intramedullary fixation device 100 is formed from a proximal portion 112, having opposed proximal and distal ends 102, 104, respectively, and a distal portion 114 having opposed proximal and distal ends 106, 108, respectively. A distal circular flange 110 is formed on the distal end 104 of the proximal portion 112, and a proximal circular flange 116 is formed on the proximal end 106 of the distal portion 114. A circular plate 118, the distal circular flange 110 and the proximal circular flange 116 are each secured together, such that the circular plate 118 is sandwiched therebetween.

In FIG. 5, circular plate 118 is shown with passages 130, 132 formed therethrough. Correspondingly, distal circular flange 110 is shown with passages 120, 122 formed therethrough, and proximal circular flange 116 is shown with passages 124, 126 formed therethrough. It should, however, be understood that these passages, for receiving corresponding screws 128, are shown for exemplary purposes only, and that any suitable number of passages may be used. Screws 128 are used to secure the circular plate 118, the distal circular flange 110 and the proximal circular flange 116 together. Additionally, as shown, circular plate 118 may have an additional central passage 134 formed therethrough for receiving an engaging rod 136, which is secured to the center of the distal circular flange 110. A similar rod may be secured to the center of the proximal circular flange 116.

In order to match the dimensions of the particular bone (e.g., the ulna), a maximum width W3 of the proximal portion 112 may be greater than a maximum width W4 of the distal portion 114. In FIGS. 4 and 5, each of the proximal portion 112, the distal portion 114, the circular plate 118, the distal circular flange 110 and the proximal circular flange 116 are shown having an exemplary size and overall shape. It should be understood that the overall contouring and relative dimensions of each of these elements are shown for exemplary purposes only, and may be varied dependent upon the particular bone, particular procedure, particular circumstances and particular patient. Additionally, it should be understood that screws 128 are shown for exemplary purposes only, and that bolts, rivets or any other suitable type of fixture may also be used to join the circular plate 118, the distal circular flange 110 and the proximal circular flange 116 together.

Figure 6:
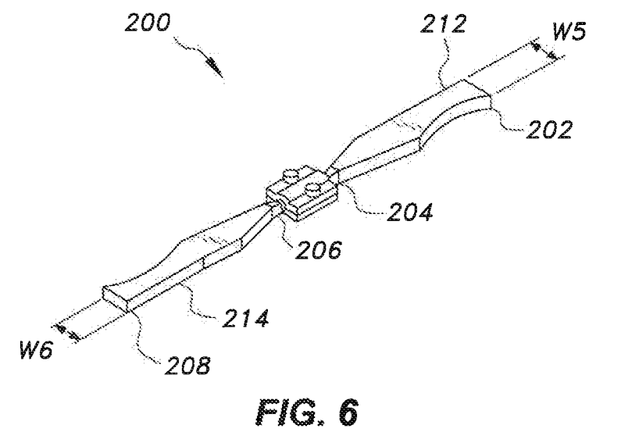
FIG. 6 is a perspective view of another alternative embodiment of the modular intramedullary fixation device.
Figure 7:
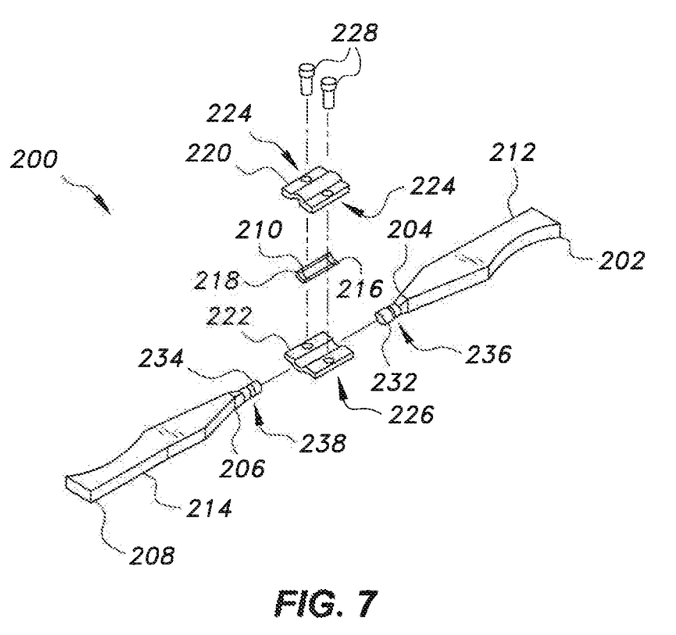
FIG. 7 is an exploded perspective view of the modular intramedullary fixation device of FIG. 6.

In the further alternative embodiment of FIGS. 6 and 7, the modular intramedullary fixation device 200 includes a proximal portion 212, having opposed proximal and distal ends 202, 204, respectively, and a distal portion 214, having opposed proximal and distal ends 206, 208, respectively. The proximal portion 212 has a distal connector 232 formed on the distal end 204. The distal connector 232 has an annular groove 236 formed therein. Similarly, the distal portion 214 has a proximal connector 234 formed on the proximal end 206. The proximal connector 234 has an annular groove 238 foraged therein.

A coupler 210 is provided, having an internal proximal rib 216 for engaging the annular groove 236 formed in the distal connector 232, and an internal distal rib 218 for engaging the annular groove 238 formed in the proximal connector 234. A pair of brackets 220, 222 clamp the coupler 210, the distal connector 232 and the proximal connector 234 therebetween. Bracket 220 has at least one passage 224 formed therethrough (shown as two passages in the non-limiting example of FIGS. 6 and 7) and, similarly, bracket 222 has at least one passage 226 formed therethrough (shown as two passages in the non-limiting example of FIGS. 6 and 7). Passages 224, 226 receive corresponding screws 228 to secure the pair of brackets 220, 222 together.

In order to match the dimensions of the particular bone (e.g., the ulna), a maximum width W5 of the proximal portion 212 may be greater than a maximum width W6 of the distal portion 214. In FIGS. 6 and 7, each of the proximal portion 212, the distal portion 214, the distal connector 232, the annular groove 236, the proximal connector 234, the annular groove 238, the coupler 210 and brackets 220, 222 are shown having an exemplary size and overall shape. It should be understood that the overall contouring and relative dimensions of each of these elements are shown for exemplary purposes only, and may be varied dependent upon the particular bone, particular procedure, particular circumstances and particular patient. Additionally, it should be understood that screws 228 are shown for exemplary purposes only, and that bolts, rivets or any other suitable type of fixture may also be used to join the pair of brackets 220, 222 together.

Figures 8, 9:
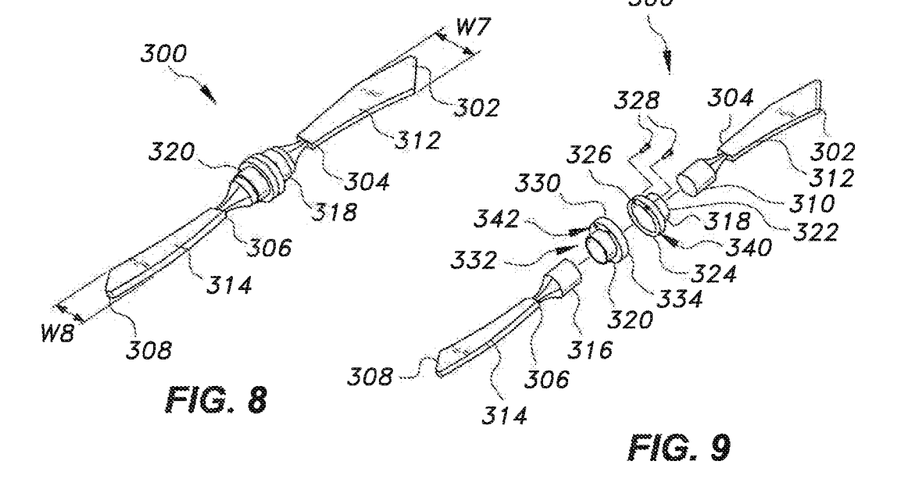
FIG. 8 is a perspective view of still another alternative embodiment of the modular intramedullary fixation device.
FIG. 9 is an exploded perspective view of the modular intramedullary fixation device of FIG. 8.

In the further alternative embodiment of FIGS. 8 and 9, the modular intramedullary fixation device 300 includes a proximal portion 312, having opposed proximal and distal ends 302, 304, respectively, with a distal connector 310 formed on the distal end 304. The modular intramedullary fixation device 300 also includes a distal portion 314, having opposed proximal and distal ends 306, 308, respectively, with a proximal connector 316 formed on the proximal end 306. A proximal collar 318, having opposed proximal and distal ends 322, 324, respectively, is provided for receiving the distal connector 310 of the proximal portion 312. A distal annular flange 326 is formed about the distal end 324 of the proximal collar 318. Similarly, a distal collar 320, having opposed distal and proximal ends 332, 334, respectively, is provided for receiving the proximal connector 316 of the distal portion 314. A proximal annular flange 330 is formed about the proximal end 334 of the distal collar 320. The distal annular flange 326 is secured to the proximal annular flange 330.

Each of the distal and proximal annular flanges 326, 330, respectively, may have at least one passage 340, 342, respectively, formed therethrough for receiving at least one screw 328 to secure the distal and proximal annular flanges 326, 330 together. In the non-limiting example of FIGS. 8 and 9, four such passages 340 and four such passages 342 are shown, although it should be understood that any suitable number of passages (and corresponding screws 328) may be used. In order to match the dimensions of the particular bone (e.g., the ulna), a maximum width W7 of the proximal portion 312 may be greater than a maximum width W8 of the distal portion 314.

In FIGS. 8 and 9, each of the proximal portion 312, the distal portion 314, the distal connector 310, the proximal connector 316, the proximal collar 318 and the distal collar 320 are shown having an exemplary size and overall shape. It should be understood that the overall contouring and relative dimensions of each of these elements are shown for exemplary purposes only, and may be varied dependent upon the particular bone, particular procedure, particular circumstances and particular patient. Additionally, it should be understood that screws 328 are shown for exemplary purposes only, and that bolts, rivets or any other suitable type of fixture may also be used to join the distal annular flange 326 and the proximal annular flange 330 together.

Figure 10:
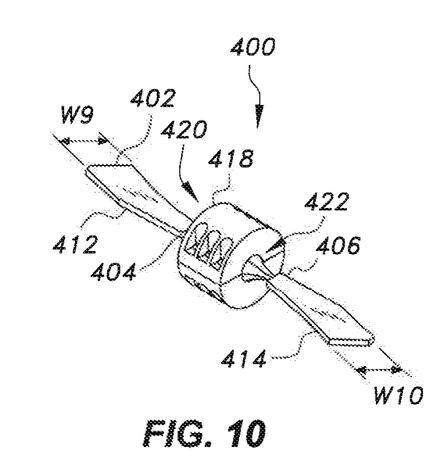
FIG. 10 is a perspective view of yet another alternative embodiment of the modular intramedullary fixation device.
Figure 11:
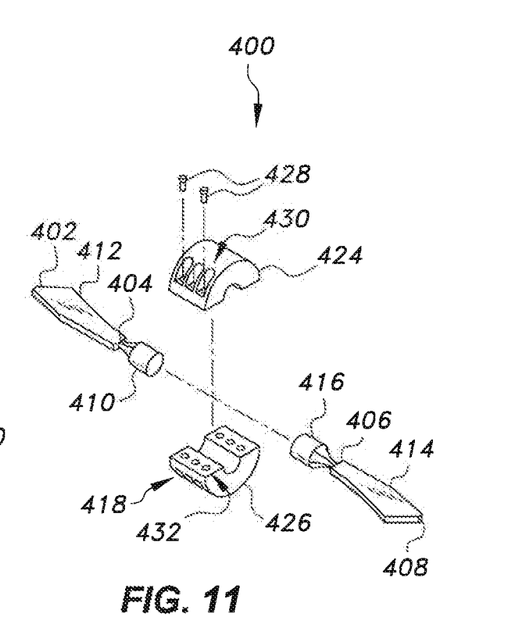
FIG. 11 is an exploded perspective view of the modular intramedullary fixation device of FIG. 10.

In the additional alternative embodiment of FIGS. 10 and 11, the modular intramedullary fixation device 400 includes a proximal portion 412, having opposed proximal and distal ends 402, 404, respectively, with a distal connector 410 formed on the distal end 404. The modular intramedullary fixation device 400 also includes a distal portion 414, having opposed proximal and distal ends 406, 408, respectively, with a proximal connector 416 formed on the proximal end 406. An annular collar 418, having opposed proximal and distal open ends 420, 422, respectively, is provided such that the proximal open end 420 receives the distal connector 410 of the proximal portion 412, and the distal open end 422 receives the proximal connector 416 of the distal portion 414, The annular collar 418 is formed from first and second semi-cylindrical portions 424, 426, respectively, secured to one another.

Each of the first and second semi-cylindrical portions 424, 426, respectively, may have at least one passage 430, 432, respectively, formed therethrough for receiving at least one screw 428 to secure the first and second semi-cylindrical portions 424, 426 together. In the non-limiting example of FIGS. 10 and 11, three such passages 430 and three such passages 432 are shown, although it should be understood that any suitable number of passages (and corresponding screws 428) may be used. In order to match the dimensions of the particular hone (e.g., the ulna), a maximum width W9 of the proximal portion 412 may be greater than a maximum width W10 of the distal portion 414.

In FIGS. 10 and 11, each of the proximal portion 412, the distal portion 414, the distal connector 410, the proximal connector 416, and the annular collar 418 are shown having an exemplary size and overall shape. It should be understood that the overall contouring and relative dimensions of each of these elements are shown for exemplary purposes only, and may be varied dependent upon the particular hone, particular procedure, particular circumstances and particular patient. Additionally, it should be understood that screws 428 are shown for exemplary purposes only, and that bolts, rivets or any other suitable type of fixture may also be used to join the first and second semi-cylindrical portions 424, 426 together.

Figure 12:
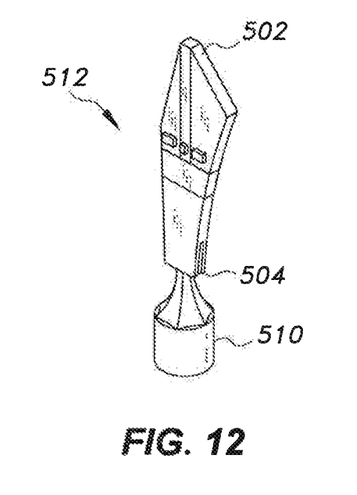
FIG. 12 is a perspective view of an alternative portion for use with the modular intramedullary fixation devices.
Figure 13:
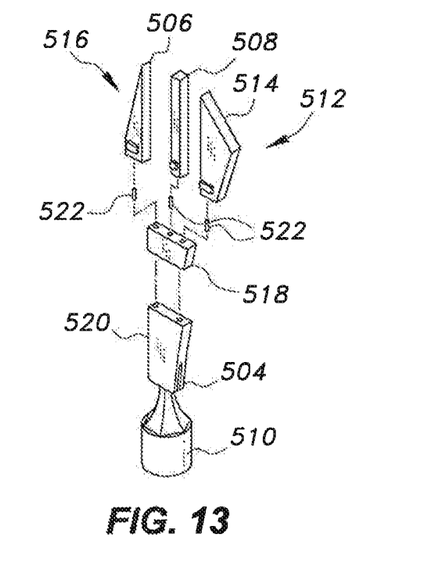
FIG. 13 is an exploded perspective view of the alternative portion of FIG. 12.

FIGS. 12 and 13 show an alternate portion 512, which has opposed proximal and distal ends 502, 504, respectively, with a distal connector 510 formed on the distal end 504. As shown in FIG. 13, a proximal region 516 of alternate portion 512 is formed from three separate panels 506, 508, 514. It should, however, be understood that proximal region 516 may be formed from any desired number of panels, and that the three panels 506, 508, 514 shown in FIG. 13 are shown for exemplary purposes only. The three panels 506, 508, 514 of proximal region 516 are secured to a central panel 518, and central panel 518 is secured to a distal panel 520. Panels 506, 508, 514, 518, 520 are all secured together by a set of internal rods 522.

In FIGS. 12 and 13, each of the panels 506, 508, 514, 518, 520, the distal connector 510, and rods 522 are shown having an exemplary size and overall shape. It should be understood that the overall contouring and relative dimensions of each of these elements are shown for exemplary purposes only, and may be varied dependent upon the particular bone, particular procedure, particular circumstances and particular patient. Additionally, it should be understood that rods 522 are shown for exemplary purposes only, and that dowels, pegs or any other suitable type of fixture may also be used to join panels 506, 508, 514, 518, 520 together.

It should be further understood that alternate portion 512 may replace proximal portion 312 and/or distal portion 314 of modular intramedullary fixation device 300, or proximal portion 412 and/or distal portion 414 of modular intramedullary fixation device 400. Further, connector 510 may be modified to resemble the circular flanges of modular intramedullary fixation device 100, allowing alternate portion 512 to replace proximal portion 112 and/or distal portion 114 of modular intramedullary fixation device 100. Similarly, connector 510 may be modified to resemble the connectors of modular intramedullary fixation device 200, allowing alternate portion 512 to replace proximal portion 212 and/or distal portion 214 of modular intramedullary fixation device 200.

Figure 14:
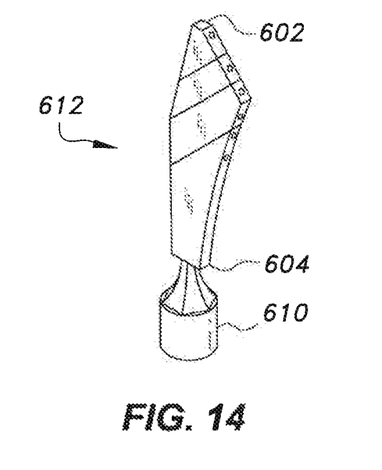
FIG. 14 is a perspective view of another alternative portion for use with the modular intramedullary fixation devices.
Figure 15:
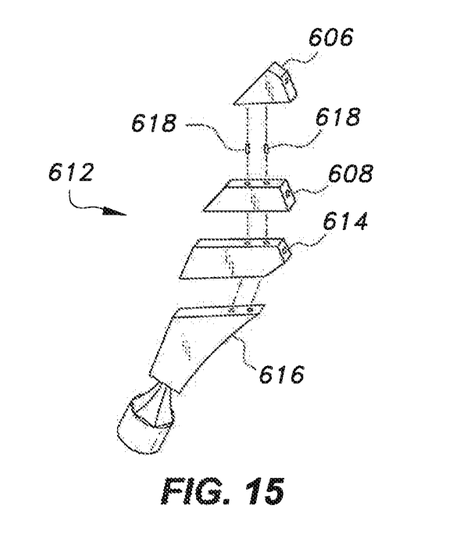
FIG. 15 is an exploded perspective view of the alternative portion of FIG. 14.

FIGS. 14 and 15 show another alternate portion 612, which has opposed proximal and distal ends 602, 604, respectively, with a distal connector 610 formed on the distal end 604. As shown in FIG. 15, a proximal panel 606 is secured to a first central panel 608, which is secured to a second central panel 614. The second central panel 614 is secured to a distal panel 616. Panels 606, 608, 614, 616 are all secured together by a set of internal rods 618.

In FIGS. 14 and 15, each of the panels 606, 608, 614, 616, the distal connector 610, and rods 618 are shown having an exemplary size and overall shape. It should be understood that the overall contouring and relative dimensions of each of these elements are shown for exemplary purposes only, and may be varied dependent upon the particular bone, particular procedure, particular circumstances and particular patient. Additionally, it should be understood that rods 618 are shown for exemplary purposes only, and that dowels, pegs or any other suitable type of fixture may also be used to join panels 606, 608, 614, 616 together.

It should be further understood that alternate portion 612 may replace proximal portion 312 and/or distal portion 314 of modular intramedullary fixation device 300, or proximal portion 412 and/or distal portion 414 of modular intramedullary fixation device 400. Further, connector 610 may be modified to resemble the circular flanges of modular intramedullary fixation device 100, allowing alternate portion 612 to replace proximal portion 112 and/or distal portion 114 of modular intramedullary fixation device 100. Similarly, connector 610 may be modified to resemble the connectors of modular intramedullary fixation device 200, allowing alternate portion 612 to replace proximal portion 212 and/or distal portion 214 of modular intramedullary fixation device 200.

Each of the previous embodiments may be implemented using a bone graft material. In the further alternative embodiment of FIG. 16, the modular intramedullary fixation device 700 may be formed from metal, such as, for example, a titanium-vanadium composite. The modular intramedullary fixation device 700 includes a proximal portion 712 having opposed proximal and distal ends 702, 704, respectively, and a proximal accordion linkage 716 to adjust the length of the proximal portion 712. The modular intramedullary fixation device 700 similarly includes a distal portion 714 having opposed proximal and distal ends 706, 708, respectively, and a distal accordion linkage 718 to adjust the length of the distal portion 714. A connector 710 is provided for connecting the proximal end 706 of the distal portion 714 to the distal end 704 of the proximal portion 712.

Figure 17A:
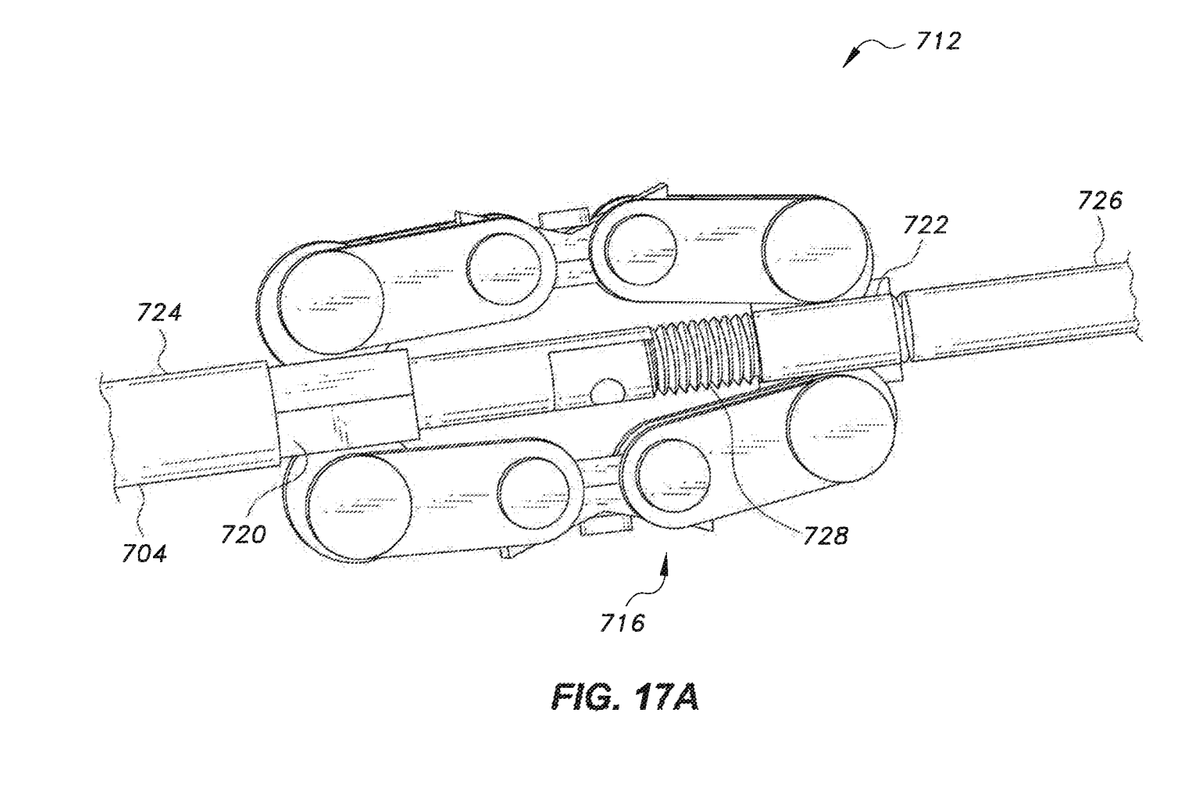
FIG. 17A is a side view of a proximal accordion linkage of the modular intramedullary fixation device of FIG. 16.

As best seen in FIG. 17A, the proximal portion 712 further includes a fixed shaft 724 and a rotating shaft 726. A first end 720 of the proximal accordion linkage 716 is secured to the fixed shaft 724 of the proximal portion 712, and a second end 722 of the proximal accordion linkage 716 is rotatably secured to the rotating shaft 726 of the proximal portion 712. The second end 722 of the proximal accordion linkage 716 may be a threaded collar in threaded engagement with a threaded portion 728 of the rotating shaft 726 of the proximal portion 712.

Figure 17B:
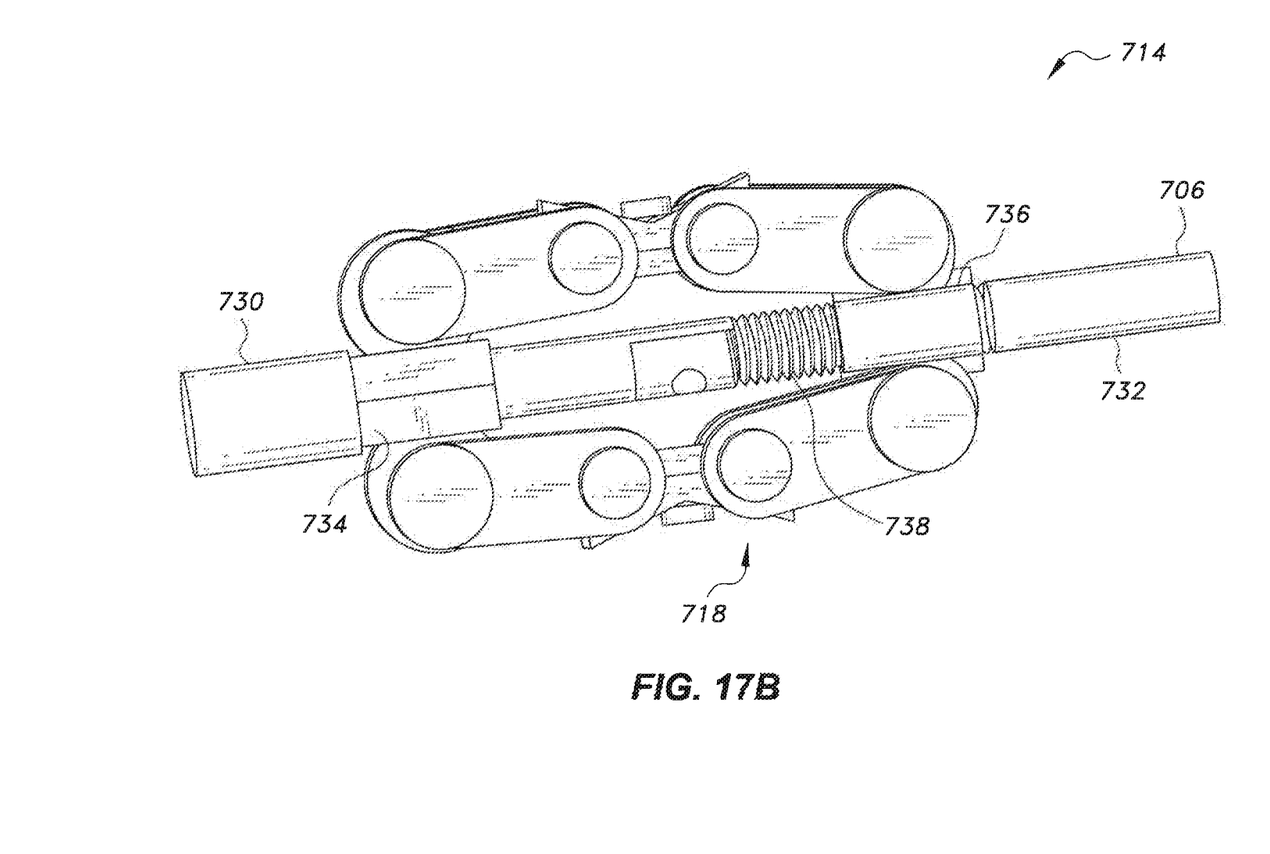
FIG. 17B is a side view of a distal accordion linkage of the modular intramedullary fixation device of FIG. 16.

Similarly, as best seen in FIG. 17B, the distal portion 714 includes a fixed shaft 730 and a rotating shaft 732. A first end 734 of the distal accordion linkage 718 is secured to the fixed shaft 730 of the distal portion 714, and a second end 736 of the distal accordion linkage 718 is rotatably secured to the rotating shaft 732 of the distal portion 714. The second end 736 of the distal accordion linkage 718 may be a threaded collar in threaded engagement with a threaded portion 738 of the rotating shaft 732 of the distal portion 714.

Figure 16:
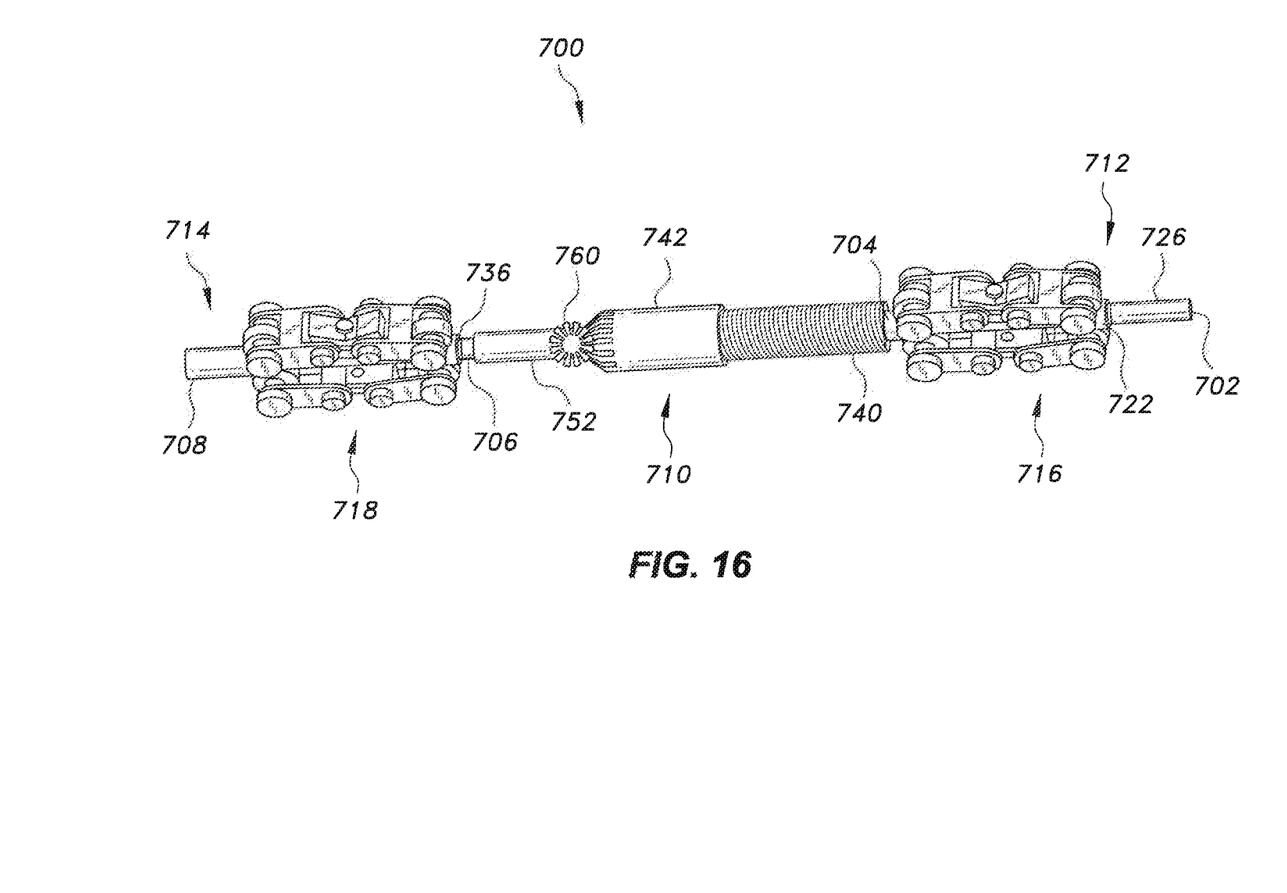
Figure 18:
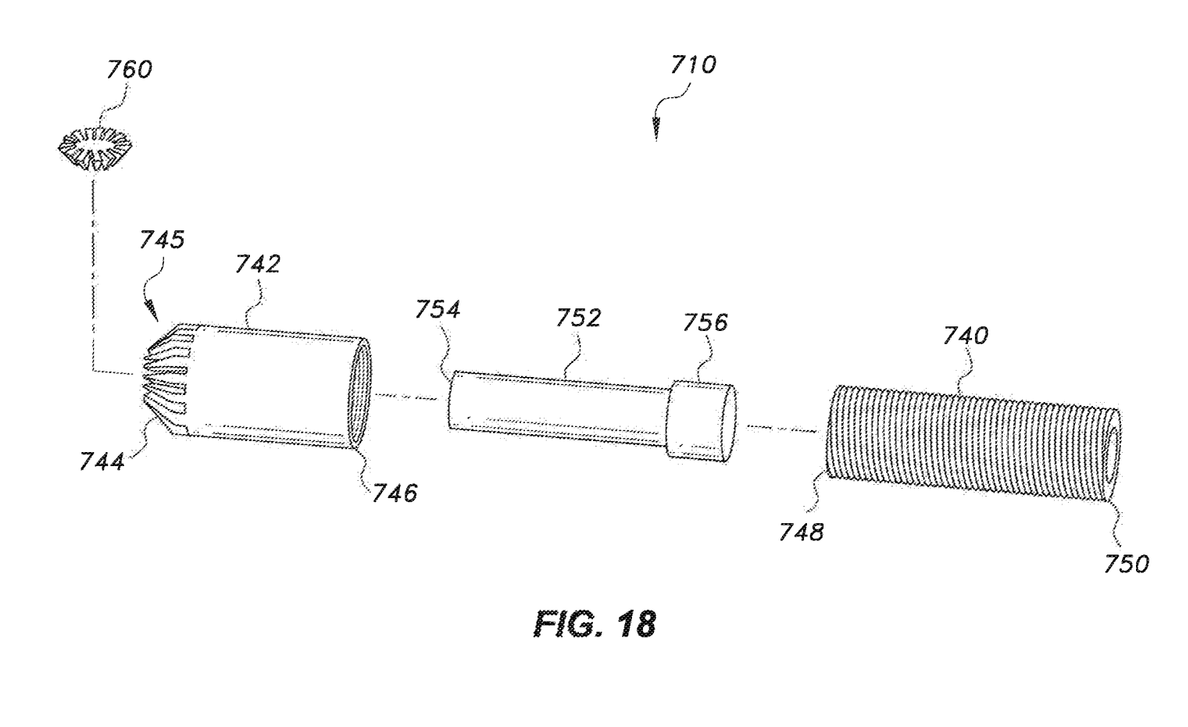
FIG. 18 is an exploded perspective view of a connector of the modular intramedullary fixation device of FIG. 16.

The connector 710 may be adjustable to adjust the overall length of the modular intramedullary fixation device 700, As shown in FIGS. 16 and 18, the connector 710 may include a threaded cylinder 740 having opposed distal and proximal ends 748, 750, respectively, with the proximal end 750 of the threaded cylinder 740 secured to the distal end 704 of the proximal portion 712. The connector 710 further includes a rotating collar 742 having opposed open distal and proximal ends 744, 746, respectively, with the rotating collar 742 having an internal threaded surface for threadedly engaging the threaded cylinder 740. The open distal end 744 of the rotating collar 742 has a plurality of teeth 745 formed therearound.

The connector 710 further includes a rod 752 partially received within the rotating collar 742 and extending through the open distal end 744. The rod 752 has opposed distal and proximal ends 754, 756, respectively, with the distal end 754 of rod 752 being secured to the proximal end 746 of the distal portion 714. A gear 760 is rotatably mounted on the rod 752, with the gear 760 engaging the plurality of teeth 745 of the rotating collar 742. The user may rotate the gear 760 to drive rotation of the rotating collar 742 which, through its threaded engagement with the threaded cylinder 740, moves with respect to the threaded cylinder 740. In this way, the user may adjust the overall length of the modular intramedullary fixation device 700.

Figure 19:
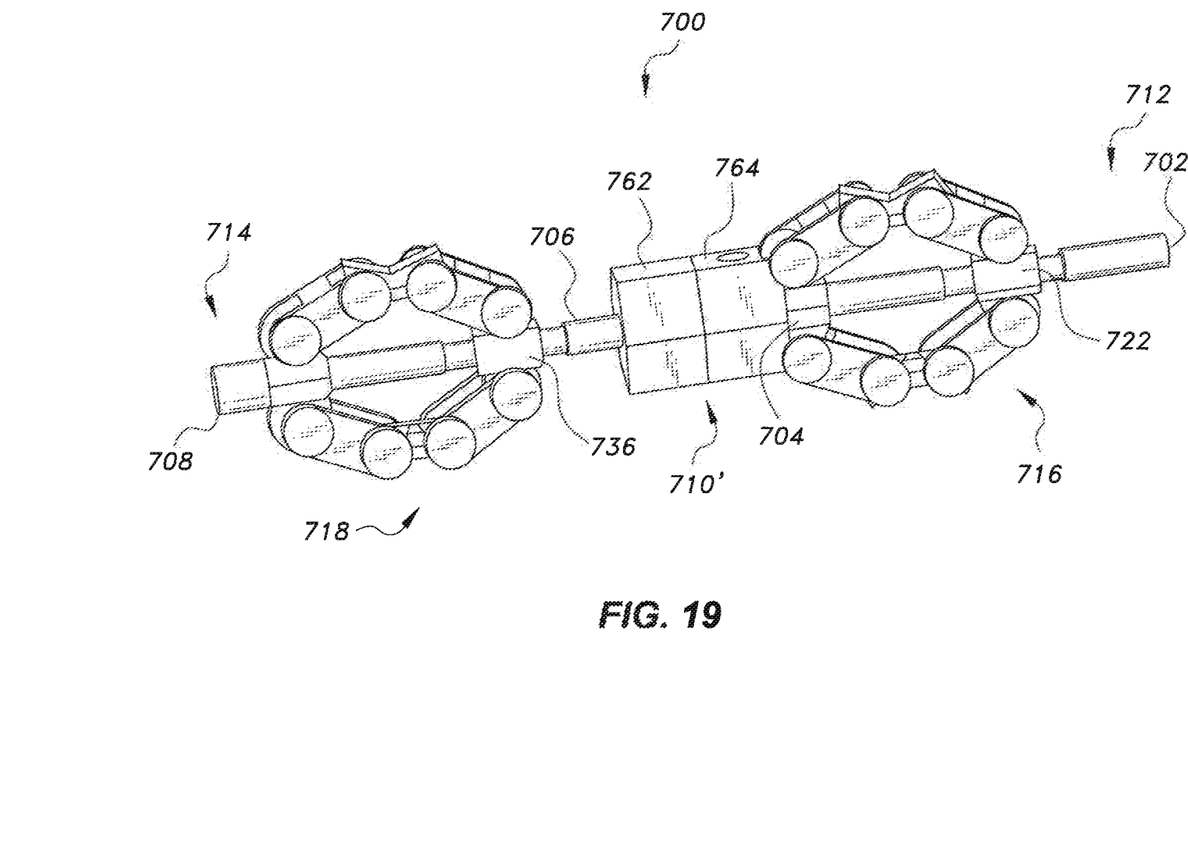
FIG. 19 is a perspective view of another alternative embodiment of the modular intramedullary fixation device.
Figure 20:
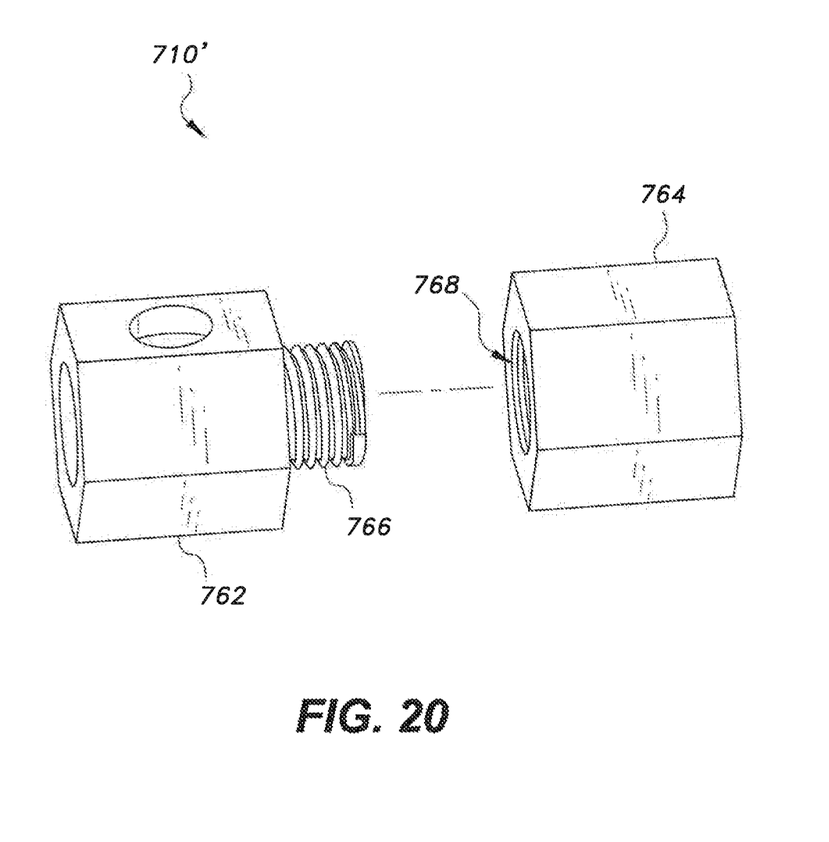
FIG. 20 is an exploded perspective view of a connector of the modular intramedullary fixation device of FIG. 19.

Alternatively, as shown in FIGS. 19 and 20, connector 710 may be replaced by alternative connector 710'. Connector 710' includes a distal connector portion 762, which is secured to the proximal end 706 of the distal portion 714, and has a threaded engaging member 766. The alternative connector 710' also includes a proximal connector portion 764, which is secured to the distal end 704 of the proximal portion 712, and has a threaded passage 768 for threadedly receiving the threaded engaging member 766.

It is to be understood that the modular intramedullary fixation devices are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:
1. A modular intramedullary fixation device, comprising:
a proximal portion having opposed proximal and distal ends;
a distal portion having opposed proximal and distal ends;
a connector for connecting the proximal portion and the distal portion together and controllably adjusting an overall length of a level of compression of an implant in a rigidly mechanically stable structure;
a threaded cylinder having opposed distal and proximal ends, the proximal end of the threaded cylinder being secured to the distal end of the proximal portion;
a rotating collar having opposed open distal and proximal ends, the rotating collar having an internal threaded surface for threadedly engaging the threaded cylinder, and wherein the open distal end of the rotating collar has a plurality of teeth formed therearound;
a rod partially received within the rotating collar and extending through the open distal end thereof, the rod having opposed distal and proximal ends, the distal end of the rod being secured to the proximal end of the distal portion; and a gear rotatably mounted on the rod, the gear engaging the plurality of teeth of the rotating collar.

2. The modular intramedullary fixation device as recited in claim 1, wherein the proximal portion further comprises a proximal accordion linkage to adjust a length, width, and height of the proximal portion as well as a distal tight fitting engaging module to engage the proximal end of the distal portion and a threadedly secured nut at the proximal end of the proximal accordion linkage; wherein the distal portion further comprises a distal accordion linkage to adjust a length, width, and height of the distal portion as well as a proximal tight fitting engaging module to engage the distal end of the proximal portion and a threadedly secured nut at the distal end of the distal accordion linkage; and wherein the connector further comprises a partially threaded cylinder acting as a guide rod spanning the implant and nuts threadedly secured to the guide rod at both the proximal end of the proximal portion and the distal end of the distal portion.

3. The modular intramedullary fixation device as recited in claim 2, wherein the proximal portion's engaging module and the distal portion's engaging module are comprised of a fixed shaft with a rotating collar and a threaded member being rotatably secured together via a gear.

4. The modular intramedullary fixation device as recited in claim 3, wherein the distal portion further comprises a fixed shaft and a rotating shaft, a first end of the distal accordion linkage being secured to the fixed shaft of the distal portion, and a second end of the distal accordion linkage being rotatably secured to the rotating shaft of the distal portion.

5. The modular intramedullary fixation device as recited in claim 4, wherein the second end of the distal accordion linkage comprises a threaded collar in threaded engagement with a threaded portion of the rotating shaft of the distal portion.

6. The modular intramedullary fixation device as recited in claim 1, wherein the connector comprises:

a distal connector portion secured to the proximal end of the distal portion, the distal connector portion having a threaded engaging member; and a proximal connector portion secured to the distal end of the proximal portion, the proximal connector portion having a threaded passage for threadedly receiving the threaded engaging member.

* * * * *